United States Patent
Richburg et al.

(10) Patent No.: US 9,717,241 B2
(45) Date of Patent: *Aug. 1, 2017

(54) INCREASED TOLERANCE OF DHT-ENABLED PLANTS TO AUXINIC HERBICIDES RESULTING FROM MOIETY DIFFERENCES IN AUXINIC HERBICIDE MOLECULAR STRUCTURES

(75) Inventors: John S. Richburg, Headland, AL (US); Terry R. Wright, Carmel, IN (US); Leon B. Braxton, Travelers Rest, SC (US); Andrew E. Robinson, Brownsburg, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 592 days.

This patent is subject to a terminal disclaimer.

(21) Appl. No.: 13/345,236

(22) Filed: Jan. 6, 2012

(65) Prior Publication Data

US 2012/0178627 A1    Jul. 12, 2012

Related U.S. Application Data

(60) Provisional application No. 61/430,693, filed on Jan. 7, 2011.

(51) Int. Cl.
*A01H 5/00*    (2006.01)
*A01H 5/10*    (2006.01)
*C12N 15/82*    (2006.01)
*A01N 39/02*    (2006.01)
*A01N 39/04*    (2006.01)

(52) U.S. Cl.
CPC ............. *A01N 39/02* (2013.01); *A01N 39/04* (2013.01)

(58) Field of Classification Search
USPC ........................................................ 800/300
See application file for complete search history.

(56) References Cited

U.S. PATENT DOCUMENTS

| | | |
|---|---|---|
| 2007/0225171 A1 | 9/2007 | Becton et al. |
| 2008/0119361 A1 | 5/2008 | Feng et al. |
| 2008/0200337 A1 | 8/2008 | Endo et al. |
| 2008/0305952 A1 * | 12/2008 | Arnevik et al. ............. 504/127 |
| 2010/0062941 A1 | 3/2010 | Hacker et al. |

FOREIGN PATENT DOCUMENTS

| | | |
|---|---|---|
| WO | 2007014758 A1 | 2/2007 |
| WO | WO 2011066384 A1 * | 6/2011 |

OTHER PUBLICATIONS

Hayashi et al, 2,4-Dichlorophenoxybutyric Acid-Resistant Mutants of Arabidopsis Have Defects in Glyoxysomal Fatty Acid beta-Oxydation, Plant Cell (1998) 10:183-185.*
Search Report for International Application No. PCT/US2012/020414, mailed Aug. 31, 2012.
Written Opinion for International Application No. PCT/US2012/020414, mailed Aug. 31, 2012.

* cited by examiner

*Primary Examiner* — Mykola V Kovalenko
(74) *Attorney, Agent, or Firm* — Eric J. Kraus; Magleby Cataxinos & Greenwood

(57) ABSTRACT

The present invention relates to a method of controlling undesirable vegetation in a field containing an auxin-herbicide-tolerant cotton crop by applying to the location where control is desired an effective amount of 2,4-DB.

4 Claims, No Drawings

INCREASED TOLERANCE OF DHT-ENABLED PLANTS TO AUXINIC HERBICIDES RESULTING FROM MOIETY DIFFERENCES IN AUXINIC HERBICIDE MOLECULAR STRUCTURES

CROSS-REFERENCE TO RELATED APPLICATION

This application claims the benefit of U.S. Provisional patent application Ser. No. 61/430,693, filed Jan. 7, 2011, the disclosure of which is hereby incorporated herein in its entirety by this reference.

FIELD OF THE INVENTION

The present invention relates to a method of controlling undesirable vegetation in a field containing an auxin herbicide tolerant cotton crop comprising applying to the location where control is desired an effective amount of 2,4-DB.

BACKGROUND OF THE INVENTION

The use of auxinic herbicides to control undesired vegetation in a field of an auxin herbicide tolerant cotton crop may cause transient injury to the auxin herbicide tolerant cotton crop that could result in delayed development. Visible transient injury may include a combination of leaf droop, leaf rolling, and petiole curvature—together referred to as epinasty. Other transient injury that may be visible 10 to 14 days after application includes leaf strapping, malformation, and epinasty on leaves. Such transient, early-season injury may result in an undesirable extension of the time for the cotton crop to mature, causing the grower to incur additional expenses and possibly reducing overall crop yield.

The present invention addresses and solves the problems associated with crop injury that results from the application of an auxinic herbicide to control undesirable vegetation in a field containing an auxin herbicide tolerant crop including delayed earliness resulting from the early-season herbicide injury.

DISCLOSURE OF THE INVENTION

An object of the present invention is a method of controlling undesirable vegetation in a field containing an auxin herbicide tolerant cotton crop comprising applying to the location where control is desired an effective amount of 2,4-DB.

Another object of the present invention is a method wherein injury to the herbicide tolerant cotton crop is reduced relative to an application of an acid equivalent amount of 2,4-D.

Additional objects and advantages of the present invention will become readily apparent to those skilled in this art from the following detailed description, wherein embodiments of the invention are described simply by way of illustrating of the best mode contemplated in carrying out the invention. As will be realized, the invention is capable of other and different embodiments, and its several details are capable of modifications in various obvious respects, all without departing from the invention. Accordingly, the description is to be regarded as illustrative in nature and not as restrictive.

DETAILED DESCRIPTION OF THE INVENTION

The present inventions will be described more fully hereinafter. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention is drawn to a method of controlling undesirable vegetation in a field containing an auxin herbicide tolerant cotton crop comprising applying to the location where control is desired an effective amount of 2,4-DB.

As used in this specification and unless otherwise indicated the term "herbicide" refers to a molecule or combination of molecules that retards or otherwise kills undesirable, unwanted plants; such as, but not limited to, deleterious or annoying weeds, broadleaf plants, grasses, and sedges; and may be used in this manner for crop protection. The phrase "effective amount" means an amount of herbicide necessary to produce an observable desired effect to reduce unwanted plant growth, including the effects of plant necrosis, plant death, growth inhibition, reproduction inhibition, inhibition of proliferation, and removal, destruction, or otherwise diminishing the occurrence and activity of undesirable, unwanted plants. Undesirable, unwanted plants include herbicide tolerant and herbicide resistant weeds such as glyphosate tolerant weeds and glyphosate resistant weeds.

"Auxin herbicide" includes herbicides having the aryloxyalkanoate chemical structure such as the phenoxyacetate auxins (e.g., 2,4-D and MCPA), phenoxybutanoate auxins (e.g., 2,4-DB and MCPB) and pyridyloxyacetate auxins (e.g., fluoroxypry and triclopyr).

Numerous auxinic herbicide tolerance genes may be employed with the plants of the invention. Cotton crops may be transformed to contain any of a family of tolerance genes (designated AAD) that code for an enzyme, aryloxyalkanoate dioxygenase (AAD), which then inactivates an auxin herbicide in planta. Such herbicide tolerance may be conferred by AAD-1 (originally from *Sphingobium herbicidovorans*), AAD-12 (originally from *Delftia acidovorans*), and AAD-13 genes as disclosed in PCT publication WO 2005/107437, PCT publication WO 2007/053482, and PCT publication US 2010/0251432 A1, respectively; these PCT publications being specifically incorporated herein by reference.

An auxinic herbicide such as 2,4-DB, is applied by a convenient method to the location where weed control is desired. The "location" is intended to include soil, seeds, and seedlings, as well as established vegetation. Herbicidal activity is exhibited by 2,4-DB when it is applied directly to the plant or to the location of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote the intended herbicidal action. Generally, it is preferred to apply 2,4-DB postemergence to relatively immature undesirable vegetation to achieve the maximum control of weeds.

Cotton (*Gossypium* spp.) is the world's most important textile fiber crop and is one of the world's most important oilseed crops. Cotton plants provide a source of human food, livestock feed, and raw material in industry. Cottonseed is pressed for cooking oil and the residual cottonseed meal is used for animal feed. Industrial uses of cotton include candlewicks, twine, paper and a multitude of fabric products.

The genus *Gossypium* is very large, currently containing 50 species. Two tetraploid species of *Gossypium* have spinnable seed fibers called lint. These two species are *G. hirsutum* (referred to as American Upland cotton) and *G. barbadense* (referred to as Pima cotton).

Cotton is a dicot plant with perfect flowers, i.e., cotton has male, pollen-producing organs and separate female, pollen receiving organs on the same flower. The cultivated cotton flower is surrounded by three triangular bracts forming what is commonly known as squares. The flower contains an open corolla with five petals, a staminal column bearing clusters of stamens and forming a tube that encloses the style. The compound pistil consists of three to five carpels with stigmas protruding above the anthers. The ovary develops into a three- to five-loculed capsule or boll. From seven to nine seeds are set within each lock or locule. On the day preceding anthesis, a twisted corolla emerges from the square. On the day of anthesis, the corolla opens and pollen shedding occurs. The corolla turns red the day following anthesis and later falls from the plant. Pollination occurs with the opening of the anthers and shedding of pollen on the stigma or with the deposit of pollen on the stigma by insects.

By "plant" is intended whole plants, plant organs (e.g., leaves, stems, roots, etc.), seeds, plant cells, propagules, embryos and progeny of the same. Plant cells can be differentiated or undifferentiated (e.g., callus, suspension culture cells, protoplasts, leaf cells, root cells, phloem cells, and pollen).

"Transgenic plants" or "transformed plants" or "stably transformed" plants, cells or tissues refer to plants that have incorporated or integrated exogenous nucleic acid sequences or DNA fragments into the plant cell. By "stable transformation" is intended that the nucleotide construct introduced into a plant integrates into the genome of the plant and is capable of being inherited by progeny thereof.

The herbicidally active compound 4-(2,4-dichlorophenoxy) butyric acid or 2,4-DB is described, for example, in Tomlin, Clive (editor) (2009) "The Pesticide Manual," Fifteenth Edition, British Crop Protection Council (BCPC), pages 306-308, and is specifically incorporated herein by reference.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface-active agents include salts of alkyl sulfates, such as diethanolammonium lauryl sulfate; alkylarylsulfonate salts, such as calciumdodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl)-sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the location of weeds generally contain about 0.0001 to about 1 weight percent active ingredient and preferably contain about 0.001 to about 0.05 weight percent.

In the methods of the present invention, the application of the 2,4-DB herbicide can be carried out, equally in pre-sowing, in pre-emergence and in post-emergence of the crop. Pre-emergence and/or early post-emergence application is preferred. "Pre-emergent" is defined as application of the herbicide during the period prior to emergence of the crop plant from the ground. "Post-emergent" is defined as application of the herbicide during the period after emergence of the crop plant from the ground where the foliage of the crop plant is contacted by the herbicide. Preferably, 2,4-DB is applied to the cotton crop post-emergence and during the vegetative growth stage of the cotton crop.

The herbicidal compounds of the present invention are often applied in conjunction with one or more other herbicides to control a wider variety of undesirable vegetation. When used in conjunction with other herbicides, the presently claimed compounds can be formulated with the other herbicide or herbicides, tank mixed with the other herbicide or herbicides or applied sequentially with the other herbicide or herbicides. Some of the herbicides that can be employed in conjunction with the compounds of the present invention include glyphosate, glufosinate, paraquat, ALS-inhibitors (e.g., sulfonylureas, imidazolinones, triazolopyrimidine sulfonanilides, etc.), HPPD inhibitors (e.g., mesotrione, isoxaflutole, etc.), PPO inhibitors (e.g., pyraflufen, fomesafen, etc.), dicamba, bromoxynil, aryloxyaklanoates and others, some of which may require genetic engineering to endow the crop with selectivity to these herbicides.

The present compositions can be applied to weeds or their location by the use of conventional ground or aerial dusters, sprayers, and granule applicators, by addition to irrigation water, and by other conventional means known to those skilled in the art.

In one aspect of the present invention, the injury to the herbicide tolerant cotton crop caused by applying an effective amount of 2,4-DB is reduced relative to an application of an effective amount of 2,4-D. Reduction of injury from herbicides advantageously reduces stress on the crop, thereby possibly reducing time for the crop to mature or even causing the grower to save expenses and increase overall crop yield.

While not intending to be bound by any theory, it is hypothesized that 2,4-DB is not a robust herbicide until it undergoes beta-oxidation in planta. This additional metabolic step and/or other factors results in increasing the AAD-transformed plant's ability to tolerate applications of 2,4-DB compared to 2,4-D. This concept can apply to all AAD-transformed crops but is particularly useful when applied to AAD-transformed crops, including cotton, that have a lower tolerance to 2,4-D.

By "injury" it is meant the percentage of foliage that is epinastic (has leaf droop, leaf rolling, petiole curvature) as visually assessed by one skilled in the art. The reduced injury from 2,4-DB relative to 2,4-D is observable within minutes after application of these herbicides and continues to be observable for an extended time period thereafter, such as from 2 hrs after application to 30 days after application, including 3 hours after application to 19 days after application and further including 6 hours after application to 24 hours after application.

The subject invention also includes transgenic aryloxyalkanoate herbicide tolerant cotton crops that comprise one or more further herbicide tolerance genes, including, but not limited to, glyphosate, ALS-(imidazolinone, sulfonylurea), aryloxyalkanoate-, HPPD-, PPO-, and glufosinate-resistance genes, so as to provide herbicide tolerant plants compatible with broader and more robust weed control and herbicide resistance management options.

Application rates of about 0.1 to about 2,240 grams acid equivalent/hectare (g ae/ha) are generally employed in postemergence operations and preferably 1 to about 1,120 g ae/ha; for pre-emergence applications, rates of about 1 to about 2,240 g ae/ha are generally employed. The higher rates designated generally give non-selective control of a broad variety of undesirable vegetation. The lower rates typically give selective control and can be employed in the location of cotton crops. In embodiments of the invention, a preferred application rate of 2,4-DB for postemergence operations is at least 280 g ae/ha, preferably from about 280 g ae/ha to about 2,240 g ae/ha.

EXAMPLES

The following examples are included to demonstrate certain preferred embodiments of the invention. These examples should not be construed as limitations to the claims. It should be appreciated by those of skill in the art that the techniques disclosed in the following examples represent specific approaches used to illustrate preferred modes for its practice. However, those of skill in the art should, in light of the present disclosure, appreciate that many changes can be made in these specific embodiments while still obtaining like or similar results without departing from the spirit and scope of the invention.

Cotton plants transformed with the AAD-1 gene (AAD-1 cotton), encode an aryloxyalkanoate dioxygenase (AAD) protein. These plants are used in the following examples to demonstrate tolerance to auxin herbicides, specifically 2,4-DB and 2,4-D. AAD-1 may also be used as a selectable marker in breeding nurseries. The AAD-1 gene, itself, for herbicide tolerance in plants was first disclosed in WO 2005/107437 (see also U.S. Pat. No. 7,838,733).

Example 1

2,4-DB and 2,4-D Provide Similar Weed Control in AAD-1-Cotton Plots

An experiment to compare the efficacies of 2,4-DB and 2,4-D to control weeds in AAD-1 cotton was conducted at nine field sites located near Greenville, Miss. (3 locations); Chula, Ga.; Macon County, Ga.; Attapulgus, Ga.; Memphis, Tenn.; Newport, Ark.; and Fresno, Calif. The experimental design was four replications per site with treatment plots in randomized complete blocks. Each plot had AAD-1-cotton plants in two rows that were 20 feet in length. Weed and cotton plants were targeted at two to six inches in height for a single-application treatment. Treatments consisted of Butyrac 200 (2,4-DB) and Weedar 64 (2,4-D) applied to plots at 560, 840, and 1120 g ae/ha. Weed species were visually assessed once per week for three weeks after herbicide application for the percentage plants (0-100%, where 0 represents no activity or a control and 100% represents death of the target plant) killed or showing severe herbicide-related injury.

Results of weed control by applications of 2,4-DB and 2,4-D in plots of AAD-1 cotton are shown in Table 1. For nearly all targeted species and for each week of measurement, greater levels of control were obtained with increasing application rates of 2,4-DB or 2,4-D, with the greatest control from 1120 g ae/ha. Therefore, based on efficacy, 1120 g ae/ha is the preferred application rate of the three rates tested to control weeds in AAD-1 cotton. At 1120 g ae/ha, control was classified as either ≤80%, >80%, or >90% of weed plants killed or seriously injured.

TABLE 1

Percentage Control of Target Weeds by 2,4-DB and 2,4-D at 1120 g ae/ha in AAD-1 Cotton

| | 2,4-DB | | | 2,4-D | | | |
|---|---|---|---|---|---|---|---|
| Species[a] | ≤80% | >80% | >90% | ≤80% | >80% | >90% | WAA[b] |
| ACCOS | | 88 | | | 90 | | 3 |
| ACNHI | | | 99 | | | 99 | 2 |
| AMAPA | | 81 | | | 89 | | 3 |
| AMAPA GLY-res | 19 | | | 26 | | | 3 |
| AMARE | | 89 | | | | 93 | 3 |
| AMASS[c] | 77 | | | | | 92 | 3 |
| CASOB | | | 100 | | | 98 | 3 |
| DEDTO | 48 | | | 53 | | | 3 |
| IAQTA | | | 99 | | | 99 | 2 |

TABLE 1-continued

Percentage Control of Target Weeds by 2,4-DB and 2,4-D at 1120 g ae/ha in AAD-1 Cotton

| Species[a] | 2,4-DB | | | 2,4-D | | | WAA[b] |
|---|---|---|---|---|---|---|---|
| | ≤80% | >80% | >90% | ≤80% | >80% | >90% | |
| IPOHG | | | 100 | | | 100 | 2 |
| IPOSS | | 99 | | | 99 | | 3 |
| MOLVE | 41 | | | 54 | | | 3 |
| RCHSC | | 99 | | | | 97 | 3 |
| SEBEX | | 89 | | | 88 | | 3 |
| SIDSP | | 84 | | | 89 | | 3 |
| SOLNI | | 89 | | | | 93 | 3 |

Abbreviations:
AAD, aryloxyalkanoate dioxygenase;
g ae/ha, grams acid equivalent per hectare;
GLY-res, glyphosate resistant;
WAA, week after application
[a]Species code maintained by the European Plant Protection Organization (http://eppt.eppo.org/index.php)
[b]Week after application to measure maximum control; n = 36 plots
[c]All Amaranthus species excluding AMAPA At an application rate of 1120 g ae/ha, 2,4-DB and 2,4-D provided equivalent control of each weed species, with the exception of Amaranthus species (AMASS) where 2,4-D noticeably exceeded 2,4-DB by 92% to 77% control. Most species were controlled at >80% by both herbicides. Species controlled at less than 80% by both herbicides were glyphosate-resistant *Amaranthus palmeri* (AMAPA GLY-res), *Desmodium tortuosum* (DEDTO), and *Mollugo verticillata* (MOLVE).

Example 2

Cotton Plants Transformed with AAD-1 have Increased Tolerance to 2,4-DB Compared to 2,4-D To evaluate the tolerance of AAD-1-cotton plants to the effects of 2,4-DB and 2,4-D herbicide compounds, the herbicides Butyrac 200 (2,4-DB) and Weedar 64 (2,4-D) were applied individually by broadcast spraying over AAD-1-cotton plants in two field experiments.

One experiment was conducted at four field locations near Greenville, Miss.; Brinson, Ga.; Memphis, Tenn.; and Fresno, Calif. The experimental design was four replications per site with treatment plots in randomized complete blocks. Each plot had AAD-1-cotton plants in two rows that were 20 feet in length. Cotton plants were targeted at two to four inches in height for single-application treatment. Treatments consisted of Butyrac 200 (2,4-DB) applied at 560, 840, 1120, 1680, and 2240 g ae/ha; and Weedar 64 (2,4-D) applied at 840 and 1120 g ae/ha. AAD-1-cotton plants were visually assessed for the percentage of foliage showing herbicide-related injury one day after application.

Results of injury on AAD-1-cotton plants from 2,4-DB or 2,4-D are shown in Table 2. At application rates of 840 g ae/ha, 2,4-DB resulted in lower (but not statistically different) levels of injury to AAD-1 cotton than was observed with 2.4-D. However, at the preferred application rate of 1120 g ae/ha, 2,4-DB resulted in significantly less injury to AAD-1 cotton than was observed with 2,4-D during the first day after application. Even at double the application rate of 2,4-DB (2240 g ae/ha) compared to 2,4-D (1120 g ae/ha), AAD-1 cotton had significantly less injury from 2,4-DB than from 2,4-D.

TABLE 2

Mean Injury 1 DAA From 2,4-DB or 2,4-D Applied Post-Emergence on AAD-1 Cotton

| | | | Credible Interval[b] | | |
|---|---|---|---|---|---|
| Herbicide | Rate (g ae/ha) | Injury (%)[a] | Lower Mean (%) | Higher Mean (%) | Significant Groups[c] |
| 2,4-DB | 560 | 2.3 | 1.2 | 4.1 | a |
| 2,4-DB | 840 | 4.1 | 2.1 | 7.9 | ab |
| 2,4-DB | 1120 | 2.8 | 1.5 | 5.3 | ab |
| 2,4-DB | 1680 | 4.5 | 2.4 | 8.2 | ab |
| 2,4-DB | 2240 | 6.3 | 4.6 | 8.6 | b |
| 2,4-D | 840 | 7.4 | 4.5 | 12.0 | bc |
| 2,4-D | 1120 | 13.0 | 9.5 | 17.7 | c |

Abbreviations: AAD, aryloxyalkanoate dioxygenase; DAA, days after application; g ae/ha, grams acid equivalent per hectare
[a]injury assessed visually as percentage of epinastic cotton-plant foliage per plot; n = 16 plots
[b]Credible intervals that do not overlap are significantly different (P = .05).
[c]Intervals followed by the same letter do not significantly differ.

Another experiment was conducted at one field location at the University of Georgia Ponder Farm, near Tifton, Ga. The experimental design was three replications with plots in randomized complete blocks. Each plot had AAD-1-cotton plants in one row that was 25 feet in length. Cotton plants were targeted at 19 inches in height (6-leaf stage) for single-application treatment. Treatments consisted of Butyrac 200 (2,4-DB) applied at 280, 560, 1120, and 2240 g ae ha; and Weedar 64 (2,4-D) applied at 560 and 1120 g ae/ha. AAD-1-cotton plants were visually assessed for the percentage of foliage showing herbicide-related injury on days—0, 1, 2, 19, and 45 after application.

Results of injury to AAD-1-cotton plants over time after application of 2,4-DB or 2,4-D are shown in Table 3. The highest levels of injury to AAD-1 cotton for all application rates were visible on the same day (day 0) of herbicide application for both 2,4-DB and 2,4-D. At the preferred application rate of 1120 g ae/ha, 2,4-DB resulted in significantly less injury than was observed with 2,4-D on days-0, 1, 2, and 19 after application. On day-45 after application, injury to AAD-1 cotton was not significantly different between 2,4-DB and 2,4-D applied at 1120 g ae/ha. Even at double the application rate of 2,4-DB (2240 g ae/ha) compared to 2,4-D (1120 g ae/ha), AAD-1 cotton had significantly less injury from 2,4-DB than from 2,4-D on days-0, 1, and 19 after application.

TABLE 3

Mean Injury Over Time From 2,4-DB or 2,4-D Applied Post-Emergence on AAD-1 Cotton

| Herbicide | Rate (g ae/ha) | Mean Injury (%)[a][b] | | | | |
|---|---|---|---|---|---|---|
| | | 0 DAA | 1 DAA | 2 DAA | 19 DAA | 45 DAA |
| 2,4-DB | 280 | 1.7 a | 0.7 a | 1.3 ab | 0.0 a | 0.0 a |
| 2,4-DB | 560 | 2.7 a | 0.0 a | 0.7 a | 0.7 a | 0.0 a |
| 2,4-DB | 1120 | 5.0 ab | 0.7 a | 1.3 ab | 0.0 a | 1.7 a |
| 2,4-DB | 2240 | 9.3 b | 2.0 a | 3.3 abc | 0.7 a | 0.0 a |
| 2,4-D | 560 | 6.7 ab | 6.7 b | 4.0 bc | 1.7 a | 3.3 a |
| 2,4-D | 1120 | 23.3 c | 14.0 c | 4.7 c | 5.0 b | 2.3 a |
| LSD (P = .05) | | 6.2 | 4.2 | 3.3 | 2.4 | 4.5 |

Abbreviations:
AAD, aryloxyalkanoate dioxygenase;
DAA, days after application;
g ae/ha, grams acid equivalent per hectare
[a]Injury assessed visually as percentage of epinastic cotton-plant foliage per plot; n = 3 plots
[b]Means followed by the same letter do not significantly differ.

Example 3

Cotton Plants Transformed With AAD-12 Have Moderately Increased Tolerance to 2,4-DB Compared to 2,4-D To evaluate the tolerance of AAD-12-cotton plants to the effects of 2,4-DB and 2,4-D herbicide compounds, the herbicides DB Straight (2,4-DB) and Weedar 64 (2,4-D) were applied individually by spraying over AAD-12-cotton plants in one greenhouse experiment. The four treatments consisted of two application rates, 1120 and 2240 g ae/ha, for each of the two herbicides. The experimental design was four replications of single AAD-12-cotton plants per treatment. The plants were grown in pots. Treatments were not randomized. Plants were at the 3- to 4-leaf stage when sprayed. The sprayed AAD-12-cotton plants were visually assessed for the percentage of foliage showing herbicide-related injury on days-0, 1, 2, 4, and 12 after application.

Results of mean injury observed on AAD-12-cotton plants from 2,4-DB or 2,4-D are shown in Table 4. From day-0 to day-4 after application (DAA), plants treated with 2,4-DB expressed lower percentages of observed foliar injury than plants treated with 2,4-D; however, the observed percentages were statistically significantly different only at the higher application rate of 2240 g ae/ha at day-2 and day-4 after application in this experiment.

TABLE 4

Mean Injury Over Time From 2,4-DB or 2,4-D Applied Post-Emergence on AAD-12 Cotton

| Herbicide | Rate (g ae/ha) | Mean Injury (%)$^{ab}$ | | | | |
|---|---|---|---|---|---|---|
| | | 0 DAA | 1 DAA | 2 DAA | 4 DAA | 12 DAA |
| 2,4-DB | 1120 | 0.0 a | 1.8 ab | 0.0 a | 1.0 b | 1.0 a |
| 2,4-DB | 2240 | 0.0 a | 0.0 b | 0.0 a | 0.5 b | 3.3 a |
| 2,4-D | 1120 | 0.5 a | 2.3 ab | 3.0 a | 3.0 b | 3.0 a |
| 2,4-D | 2240 | 1.3 a | 4.3 a | 3.8 a | 6.8 a | 3.0 a |
| Tukey's HSD (P = .05) | | 2.8 | 3.0 | 4.5 | 3.4 | 3.9 |

Abbreviations:
AAD, aryloxyalkanoate dioxygenase;
DAA, days after application;
g ae/ha, grams acid equivalent per hectare;
HSD, honestly significant difference
$^a$Injury assessed visually as percentage of epinastic cotton-plant foliage; n = 4 plants
$^b$Means followed by the same letter do not significantly differ.

Example 4

Cotton Plants Transformed with AAD-13

A cotton cell may be transformed with AAD-13 to produce a cotton plant with tolerance to 2,4-DB and 2,4-D that is similar to the tolerance provided by the AAD-1 or AAD-12 genes.

Cotton transformed with AAD-13 may be utilized using the same techniques previously described in Example #7 of US 2010/0251432 [PCT/US08/63212 (Lira et al.)], hereinafter incorporated by reference.

In the previous descriptions, numerous specific details are set forth, such as specific materials, structures, chemicals, processes, etc., to provide a better understanding of the present invention. However, the present invention can be practiced without resorting to the details specifically set forth. In other instances, well-known processing structures have not been described in detail in order not to unnecessarily obscure the present invention.

Only the preferred embodiment of the invention and but a few examples of its versatility are shown and described in the present disclosure. It is to be understood that the present invention is capable of use in various other combinations and environments and is capable of changes or modifications within the scope of the inventive concept as expressed herein.

We claim:

1. A method for controlling undesirable vegetation in a field containing an aryloxyalkanoate auxin herbicide-tolerant cotton crop while limiting epinastic herbicide injury to the crop, the method comprising:
   applying to a location in the crop where control is desired, post-emergent and during the vegetative stage of growth of the plants of the herbicide tolerant cotton crop, an herbicidal treatment consisting of at least 1120 grams acid equivalent/hectare (g ae/ha) 2,4-DB,
   wherein no other herbicide is applied to the crop,
   wherein the plants of the herbicide tolerant cotton crop comprise a gene coding for AAD-1 (aryloxyalkanoate dioxygenase-1), and
   wherein the percentage of the foliage of the herbicide tolerant cotton plants that is epinastic one day after the application of 2,4-DB is less than about 8.6%.

2. The method according to claim 1, wherein the transgenic aryloxyalkanoate auxin herbicide-tolerant cotton crop comprises at least one further herbicide tolerance gene.

3. A method for controlling undesirable vegetation in a field containing an aryloxyalkanoate auxin herbicide-tolerant cotton crop while limiting epinastic herbicide injury to the crop, the method comprising:
   applying to a location in a cotton crop containing undesirable vegetation where control of the vegetation is desired, post-emergent and during the vegetative stage of growth of the plants of the herbicide tolerant cotton crop, an herbicidal treatment consisting of at least 1120 grams acid equivalent/hectare (g ae/ha) 2,4-DB,
   wherein no herbicide other than 2,4-DB is applied to the crop,
   wherein the plants of the herbicide tolerant cotton crop comprise a gene coding for AAD-1 (aryloxyalkanoate dioxygenase-1),
   wherein the undesirable vegetation comprises a weed species selected from the group consisting of *Desmodium tortuosum* (DEDTO), *Mollugo verticallata* (MOLVE), *Acalypha ostryifolia* (ACCOS), *Acanthospermum hispidum* (ACNHI), *Cassia obtusifolia* (CASOB), *Ipomoea* sp. (IPOSS), *Ipomoea hederacea* (IPOHG), *Richardia scabra* (RCHSC), and *Sesbania exaltata* (SEBEX), and
   wherein the percentage of the foliage of the herbicide tolerant cotton plants that is epinastic one day after the application of 2,4-DB is less than about 8.6%.

4. The method according to claim 3, wherein the undesirable vegetation comprises a weed species selected from the group consisting of *Acalypha ostryifolia* (ACCOS), *Acanthospermum hispidum* (ACNHI), *Cassia obtusifolia* (CASOB), *Ipomoea* sp. (IPOSS), *Ipomoea hederacea* (IPOHG), *Richardia scabra* (RCHSC), and *Sesbania exaltata* (SEBEX).

* * * * *